United States Patent [19]

Wallach

[11] Patent Number: 5,032,457
[45] Date of Patent: Jul. 16, 1991

[54] PAUCILAMELLAR LIPID VESICLES USING CHARGE-LOCALIZED, SINGLE CHAIN, NONPHOSPHOLIPID SURFACTANTS

[75] Inventor: Donald F. H. Wallach, Brookline, Mass.

[73] Assignee: Micro Vesicular Systems, Inc., Nashua, N.H.

[21] Appl. No.: 410,608

[22] Filed: Sep. 21, 1989

Related U.S. Application Data

[63] Continuation-in-part of Ser. No. 157,571, Mar. 3, 1988, Pat. No. 4,911,928, which is a continuation-in-part of Ser. No. 78,658, Jul. 28, 1987, Pat. No. 4,855,090, which is a continuation-in-part of Ser. No. 25,525, Mar. 13, 1987, abandoned, and Ser. No. 124,824, Nov. 25, 1987, Pat. No. 4,917,951.

[51] Int. Cl.$^5$ .................... A61K 9/127; B01J 13/02
[52] U.S. Cl. .................. 428/402.2; 264/4.1; 424/450; 436/829
[58] Field of Search ............ 364/4.1; 428/402.2; 424/450; 436/829

[56] References Cited

U.S. PATENT DOCUMENTS

| | | | |
|---|---|---|---|
| 3,069,370 | 12/1962 | Jensen et al. | 523/200 |
| 3,372,201 | 5/1968 | Leary et al. | 568/618 |
| 3,957,971 | 5/1976 | Oleniacz | 424/70 |
| 4,075,131 | 2/1978 | Sterling | 252/542 |
| 4,182,330 | 1/1980 | Michaels | 128/260 |
| 4,191,928 | 3/1990 | Wallach | 264/4.1 X |
| 4,217,344 | 8/1980 | Vanlerberghe et al. | 424/60 |
| 4,235,871 | 11/1980 | Papahadjopoulos et al. | 424/450 |
| 4,241,046 | 12/1980 | Papahadjopoulos | 424/450 X |
| 4,247,411 | 1/1981 | Vanlerberghe et al. | 424/450 X |
| 4,348,329 | 9/1982 | Chapman | 260/463 |
| 4,356,167 | 10/1982 | Kelly | 424/450 |
| 4,377,567 | 3/1983 | Geho | 424/1.1 |
| 4,536,324 | 8/1985 | Fujiwara | 252/311 |
| 4,544,545 | 10/1985 | Ryan et al. | 424/1.1 |
| 4,551,288 | 11/1985 | Kelly | 264/4.6 |
| 4,610,868 | 9/1986 | Fountain et al. | 424/1.1 |
| 4,666,711 | 5/1987 | Vanlerberghe et al. | 424/70 |
| 4,684,625 | 8/1987 | Eppstein | 514/19 |
| 4,695,554 | 9/1987 | O'Connell et al. | 436/528 |
| 4,725,442 | 2/1988 | Haynes | 424/490 |
| 4,731,210 | 3/1988 | Weder et al. | 264/4.3 |
| 4,744,989 | 5/1988 | Payne et al. | 424/490 |
| 4,762,915 | 8/1988 | Kung et al. | 264/4.1 X |
| 4,772,471 | 1/1981 | Vanlerberghe et al. | 424/450 |
| 4,789,633 | 12/1988 | Huang et al. | 264/4.1 X |
| 4,832,872 | 5/1989 | Scandel | 252/547 |

FOREIGN PATENT DOCUMENTS

| | | |
|---|---|---|
| 0032578 | 7/1981 | European Pat. Off. . |
| 0167825 | 1/1986 | European Pat. Off. . |
| 59-106423 | 6/1984 | Japan . |
| 61-207324 | 9/1986 | Japan . |
| 1539625 | 1/1979 | United Kingdom . |
| 2078543 | 1/1982 | United Kingdom . |
| 2079179 | 1/1982 | United Kingdom . |
| 2147263 | 5/1985 | United Kingdom . |
| 2166107 | 4/1986 | United Kingdom . |
| 8706499 | 11/1987 | World Int. Prop. O. . |

OTHER PUBLICATIONS

Murakami et al., *J. Org. Chem* 47:2137–2144 (1982).
McCutcheon, *Detergents & Emulsifiers*, 1973 North American Edition, (NJ:Allured Pub. Co., 1973), p. 27.
McCutcheon, *Emulsifiers & Detergents*, 1982 North American Edition, (NJ:Allured Pub. Co., 1982) pp. 71 & 77.
Gregoriadis, Gregory, Ph.D., 295 *N. E. J. Med.* 13:704–710 (1976).
Bangham et al., *J. Mol. Biol.* 13:238–252 (1965).
Szoka et al., *Proc. Nat'l Acad. Sci. USA* 75:4194–4198.
Baillie et al., *J. Pharm. Pharmacol.* 37:863–868 (1985).
Puisieux et al., "Problems Technologiques Poses par l'Utilisation des Liposomes". . . 1985 (no translation). pp. 73–113.
Baillie et al., *J. Pharm. Pharmacol.* 38:502–404 (1986).
Dousset et al., "Methods de Prepation des Lipsomes," 1985, (no translation) pp. 41–71.
Ribier et al., *Colloids and Surfaces* 10:155–161 (1984).
Handjani-Villa, "les Niosomes," 1985, (No Translation).

Primary Examiner—Richard D. Lovering
Attorney, Agent, or Firm—Lahine & Cockfield

[57] ABSTRACT

Disclosed are paucilamellar lipid vesicles made of single chain nonphospholipid anionic or zwitterionic surfactants and a method of their manufacture. The preferred vesicle forming materials are single chain sarcosinamides having 12–20 carbon chains and single chain betaines. The vesicles are formed rapidly and can be used to encapsulate aqueous or oily solutions.

32 Claims, No Drawings

PAUCILAMELLAR LIPID VESICLES USING CHARGE-LOCALIZED, SINGLE CHAIN, NONPHOSPHOLIPID SURFACTANTS

REFERENCE TO RELATED APPLICATIONS

This application is a continuation-in-part of U.S. patent application Ser. No. 157,571, filed Mar. 3, 1988, entitled "Paucilamellar Lipid Vesicles", now U.S. Pat. No. 4,911,928 which is a continuation-in-part of U.S. patent application No. 078,658, filed July 28, 1987, now U.S. Pat. No. 4,855,090, which itself is a continuation-in-part of U.S. patent application Ser. No. 025,525, filed Mar. 13, 1987, now abandoned, both entitled "Method of Producing High Aqueous Volume Multilamellar Vesicles," and U.S. patent application Ser. No. 124,824, filed Nov. 25, 1987, now U.S. Pat. No. 4,917,951 entitled "Lipid Vesicles Formed of Surfactants and Steroids."

This application is also related to U.S. patent application Ser. No. 163,806, entitled "Method and Apparatus for Producing Lipid Vesicles" now U.S. Pat. No. 4,895,452.

BACKGROUND OF THE INVENTION

The present invention relates to the production of paucilamellar lipid vesicles having charge-localized, single chain nonphospholipid zwitterionic or anionic surfactants as the primary structural material of their lipid bilayers. More particularly, the present invention relates to a method of producing these paucilamellar lipid vesicles having a large aqueous or organic liquid filled amorphous central cavity, as well as the vesicles themselves.

Lipid vesicles are substantially spherical structures made of materials having a high lipid content, e.g., surfactants or phospholipids. The lipids of these spherical vesicles are organized in the form of lipid bilayers. The lipid bilayers encapsulate an aqueous volume which is either interspersed between multiple onion-like shells of lipid bilayers, forming a classic multilamellar lipid contained within an amorphous central cavity. Common lipid vesicles having an amorphous central cavity filled with aqueous medium are the unilamellar lipid vesicles. Large unilamellar vesicles ("LUV"'s) generally have a diameter greater than about 1 μ while small unilamellar lipid vesicles ("SUV"'s) generally have a diameter of less than 0.2 μ.

Paucilamellar lipid vesicles ("PLV"'s) are a hybrid having features of both MLV's and LUV's. PLV's are characterized by having 2–10 peripheral bilayers surrounding a large, unstructured central cavity.

The potential utility of liposomes is widely recognized. Their ability to encapsulate aqueous volumes and/or lipophilic material makes them attractive devices for transporting a whole spectrum of molecules, including macromolecules and drugs, vaccines, and other therapeutic compositions. In addition, it is possible to encapsulate supramolecular structures such as viruses using classes of liposomes. Some types of vesicles have shown an ability to act as adjuvants or as carriers or storage devices for oil-based materials.

Each type of lipid vesicle appears to have certain uses for which it is best adapted. For example, the multiple onion-like lipid bilayers of classic MLV's provide this lipid vesicle with increased durability and protection from enzymatic degradation. The multiple shells greatly diminish the volume available for aqueous solutions to be encapsulated within the bilayers of the MLV. MLV's have heretofore been deemed most advantageous for carrying lipophilic materials which can be incorporated in their bilayers. However, there is a maximum amount of lipophilic material that can be incorporated into MLV bilayers, beyond which the bilayers become unstable and these vesicles break down. In contrast, the single shell of LUV's allow the encapsulation of a larger volume of aqueous material but because of their single lipid bilayer structure, LUV's are not as physically durable as MLV's. SUV's have neither the lipid or aqueous volumes of MLV's or LUV's, but because of their small size have easiest access to cells and tissues.

PLV's appear to have advantages as transport vehicles for many uses as compared with the other types of lipid vesicles. In particular, because of their large unstructured central cavity, PLV's are easily adapted for transport of large quantities of aqueous-based materials. However, their multiple lipid bilayers provide PLV's with the ability to carry lipophilic material in their bilayers as well as with additional physical strength and resistance to degradation as compared with the single lipid bilayer of the LUV. In addition, as illustrated in the present application and U.S. patent application Ser. No. 157,571, now U.S. Pat. No. 4,911,928, the disclosure of which is incorporated herein by reference, the central cavity of the PLV's can be filled wholly or in part with an apolar oil or wax and then can be used as a vehicle for the transport or storage of hydrophobic materials. Thus, the amount of hydrophobic material which can be transported by PLV's with an apolar core is much greater than can be transported by classic MLV's.

Early lipid vesicle or liposome studies used phospholipids as the lipid source for bilayers, primarily because phospholipids are the principal structural components of natural membranes. However, there are a number of problems associated with using phospholipids as artificial membranes. First, isolated phospholipids are subject to degradation by a large variety of enzymes. Second, the most easily available phospholipids are those from natural sources, e.g., egg yolk lecithin, which contain polyunsaturated acyl chains that are subject to autocatalyzed peroxidation. When peroxidation occurs, the lipid structure breaks down, causing premature release of encapsulated materials and the formation of toxic peroxidation byproducts. This problem can be avoided by hydrogenation but hydrogenation is an expensive process, thereby raising the cost of the starting materials. Cost is a third problem associated with the use of phospholipids on a large scale. The high cost of a kilogram of egg yolk lecithin pure enough for pharmacological liposome production places a severe limitation on the use of phospholipids as a source material.

It is now known that commercially available surfactants may be used to form the lipid bilayer in a variety of lipid vesicles. (See, e.g., U.S. Pat. No. 4,217,344, U.S. Pat. No. 4,855,090, and U.S. patent application Ser. No. 157,571 now U.S. Pat. No. 4,911,928). Both surfactants and phospholipids are amphiphiles, having at least one lipophilic acyl or alkyl group attached to a hydrophilic head group. The head groups are attached to one or more lipophilic chains by ester, ether or amide linkages. Commercially available surfactants include the BRIJ family of polyoxyethylene fatty acid ethers, the SPAN sorbitan alkyl esters, and the TWEEN polyoxyethylene sorbitan fatty acid esters, all available from ICI Americas, Inc., of Wilmington, Delaware. Unlike phospholipids, these surfactants are generally nonionic, and addition of a charge-producing amphiphile is usually required to prevent flocculation and to increase the degree of encapsulation of water-soluble substances. Addition of a charge-producing amphiphile is not required if the primary wall lipid is anionic—as in the case of sarcosinamides.

In addition, the presence of a sterol or sterol-like molecule in the lipophilic phase used to create the lipid bilayer has often been found to be important for increasing the stability of the bilayer and hence the vesicle.

In 1982, Murakami et al. disclosed the preparation of small (0.05–0.2 μ), single- or multiple-walled vesicles capable of encapsulating aqueous volumes, using cationic and zwitterionic double chain amphiphiles synthesized to mimic the structure of naturally occurring phospholipids. The aqueous-carrying capacity of these vesicles is unknown as is their structure and stability. Murakami does not mention the possibility of oil encapsulation or single chain varieties of these ionic lipids.

The use of anionic or zwitterionic surfactants as cleaning or conditioning agents in cleansers such as shampoos is well documented in the art (see e.g., U.S. Pat. No. 4,075,131 and U.S. Pat. No. 4,832,872). However, in their present formulation in cleanser compositions, these surfactants are not present in vesicle form.

Recently an improved method for creating large aqueous volume MLV's and PLV's using commercially available, synthethic, nonionic surfactants has been discovered. U.S. Pat. No. 4,855,090, and U.S. patent application Ser. No. 157,571 now U.S. Pat. No. 4,911,928, disclose this new method which has the advantage of being faster and more cost-efficient than previous methods. This improved method of creating PLV's and large aqueous volume MLV's, which is applicable to only certain surfactants, forms vesicles in less than a second rather than the minutes or hours of classical techniques. Moreover, the improved method allows vesicles to be formed without the use of solvents and without the formation of a separable lamellar phase. These techniques, and the devices to utilize them, have only been described in the aforementioned patents, as well as the related applications. In contrast, the classic methods for producing multilamellar lipid vesicles are well-documented in the art. See for example Gregoriadis, G., ed. *Liposome Technology* (CRC, Boca Raton, FL), Vols. 1–3 (1984), and Dousset and Douste-Blzay (in *Les Liposomes*, Puisieux and Delattre, ed., *Techniques et Documentation Lavoiser*, Paris, pp. 41–73 (1985).

No matter how the MLV's or PLV's are formed, once made it is necessary to determine the effectiveness of the process. Two measurements commonly used to determine the effectiveness of encapsulation of materials in lipid vesicles are the encapsulated mass and captured volume. The encapsulated mass is the mass of the substance encapsulated per unit mass of the lipid and is often given as a percentage. The captured volume is defined as the amount of the aqueous phase trapped inside the vesicle divided by the amount of lipid in the vesicle structure, normally given in ml liquid/g lipid.

The methods and materials disclosed herein for producing paucilamellar lipid vesicles formed of single chain charge-localized nonphospholipid zwitterionic or anionic surfactants all yield stable vesicles capable of encapsulating aqueous or oil volumes.

Accordingly, an object of the invention is to provide stable paucilamellar lipid vesicles from charge-localized non-phospholipid single chain surfactants.

Another object of the invention is to provide a method for producing such paucilamellar lipid vesicles which is rapid and uses relatively inexpensive materials.

A further object of the invention is to provide a vehicle for the transport of aqueous or oil-soluble materials formed essentially of charge-localized nonphospholipid single chain zwitterionic or anionic surfactants.

These and other objects and features of the invention will be apparent from the detailed description and the claims.

SUMMARY OF THE INVENTION

The present invention features paucilamellar lipid vesicles whose primary lipid bilayer structural material is charge-localized single chain nonphospholipid material such as betaines or anionic sarcosinamides, for use as carriers of hydrophilic or hydrophobic materials, and a method for their manufacture. A "charge-localized" molecule, as defined herein is a molecule containing a separation of charge so that a positive charge is located at one portion of the molecule while a negative charge is located at a different portion—for example, a zwitterionic or an ionic molecule which has an associated counter-ion.

The method of the present invention for making paucilamellar lipid vesicles has the steps of forming a lipophilic phase of a single chain nonphospholipid zwitterionic or anionic surfactant and any other lipid soluble materials being incorporated in the bilayers of the vesicle which are dissoluble in the surfactant. Zwitterionic paucilamellar lipid vesicles are preferably made from surfactants selected from the group consisting of betaines having the structure

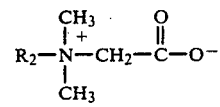

where $R_2$ is a long chain fatty acid ester. A preferred betaine is oleoyl propyl betaine, where $R_2$ has the structure

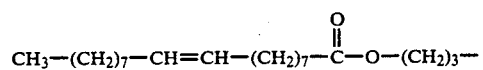

Anionic surfactants preferred in the invention are selected from the group consisting of sarcosinamides having the formula

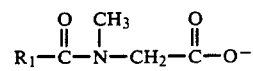

where

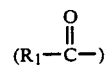

is the carbonyl derivative of a long chain fatty acid having 12 to 20 carbon atoms. Preferred sarcosinamides include the sarcosinamides of lauric acid, oleic acid, or methyl-sarcosinamides of mixed fatty acids having 14-20 carbon atoms, e.g., the methyl-sarcosinamides of fraction 3 of coconut oil.

The lipophilic phase, which may contain charge-producing materials and/or sterols such as cholesterol or hydrocortisone or their analogs and derivatives, is blended with an aqueous phase consisting of an aqueous buffer and any aqueous-soluble materials to be encapsulated, under shear mixing conditions, to form the paucilamellar lipid vesicles. "Shear mixing" is defined as the mixing of the lipophilic phase with the aqueous phase under turbulent or shear conditions which provide adequate mixing to hydrate the lipid and form lipid vesicles. "Shear mixing" is achieved by liquid shear which is substantially equivalent to a relative flow rate for the combined phases of about 5-30 m/s through a 1 mm orifice.

The invention further features the encapsulation of oil-soluble or oil-suspendable materials within these paucilamellar lipid vesicles. This procedure commences with dispersing the material to be encapsulated in an oil or wax, forming an oily phase. The oil or wax is a water immiscible oily solution selected from a group consisting of oils, waxes, natural and synthetic triglycerides, acyl esters, and petroleum derivatives, and their analogs and derivatives. The terms "disperse" or "dispersion" as used herein include dissolution or forming a suspension or colloid to yield a flowable phase. The oily phase containing the oil-dispersible material is mixed with the lipid phase and the combined oil-lipid phase is blended under shear mixing conditions with the aqueous phase. Surfactants useful in the encapsulation process are the same as those used to make the aqueous-filled paucilamellar lipid vesicles described above.

In order to achieve the proper blending necessary to form paucilamellar lipid vesicles of this invention, all of the materials are normally in a flowable state. This is easily achieved by elevating the temperature of the lipophilic phase in order to make it flowable followed by carrying out the shear mixing between the lipophilic phase and the aqueous phase at a temperature such that both phases are liquids. The surfactants of this invention are such that only gentle heating is required to obtain flowability. While it is often desirable to use the same temperature for both phases, this is not always necessary.

DETAILED DESCRIPTION OF PREFERRED EMBODIMENTS

The present invention relates to the production of zwitterionic and anionic paucilamellar lipid vesicles and the zwitterionic or anionic paucilamellar lipid vesicles themselves. These lipid vesicles, which have a single chain, nonphospholipid charge-localized surfactant material as their primary structural component, are characterized by having 2-10 lipid bilayers with a small aqueous volume separating each substantially spherical lipid shell, surrounding a large amorphous central cavity. The cavity can be filled with an oil (including a wax), an aqueous-based solution or some mixture thereof.

For certain uses, the incorporation of a charge-producing amphiphile or a sterol may be desired. Preferred charge-producing amphiphiles include dicetyl phosphate, cetyl sulfate, long chain fatty acids, retinoic acid, carboxylic acids, quarternary ammonium compounds, and derivates thereof. Cholesterol or one of its derivatives is a preferred sterol.

The paucilamellar lipid vesicles can be made by a variety of devices which provides sufficiently high shear for shear mixing. There are a large variety of these devices available on the market including a microfluidizer such as is made by Biotechnology Development Corporation, a "French"-type press, or some other device which provides a high enough shear force and the ability to handle heated, semiviscous lipids. If a very high shear device is used, it may be possible to microemulsify powdered lipids, under pressure, at a temperature below their normal melting points and still form the lipid vesicles of the present invention.

A device which is particularly useful for making the lipid vesicles of the present invention has been developed by Micro Vesicular Systems, Inc., Vineland, New Jersey and is further described in U.S. patent application Ser. No. 163,806, now U.S. Pat. No. 4,895,452. Briefly, this device has a substantially cylindrical mixing chamber with at least one tangentially located inlet orifice. One or more orifices lead to a reservoir of the lipophilic phase, mixed with an oil phase if lipid-core PLV's are to be formed, and at least one of the other orifices is attached to a reservoir for the aqueous phase. The different phases are driven into the cylindrical chamber through pumps, e.g., positive displacement pumps, and intersect in such a manner as to form a turbulent flow within the chamber. The paucilamellar lipid vesicles form rapidly, e.g., in less than 1 second, and are removed from the chamber through an axially located discharge orifice. In a preferred embodiment, there are four tangentially located inlet orifices and the lipid and aqueous phases are drawn from reservoirs, through positive displacement pumps, to alternating orifices. The fluid stream through the tangential orifices is guided in a spiral flow path from each inlet or injection orifice to the discharge orifice. The flow paths are controlled by the orientation or placement of the inlet or injection orifices so as to create a mixing zone by the intersection of the streams of liquid. The pump speeds, as well as the orifice and feed line diameters, are selected to achieve proper shear mixing for lipid vesicle formation. As noted, in most circumstances, turbulent flow is selected to provide adequate mixing.

The invention, and its many uses, will be more apparent from the following, non-limiting examples.

EXAMPLE 1

In this example three different sarcosinamides are tested for their ability to form paucilamellar lipid vesicles in the presence and absence of cholesterol and oleic acid, and for their ability to encapsulate an aqueous solution.

Table 1 lists the materials used and the results. The presence or absence of cholesterol (C) is indicated by a positive (+) or negative (−) sign. All sarcosinamides are obtained from R. T. Vanderbilt Company, Inc. (Norwalk, CT): Vanseal LS ("LS") is the sarcosinamide of lauric acid, Vanseal OS ("OS") is the sarcosinamide of oleic acid, and Vanseal CS ("CS") is a methyl-sarcosinamide of fatty acids derived from coconut oil—a mixture of mostly saturated $C_{14}$-$C_{20}$ carboxylic acids. The reactions are carried out in solutions having a pH such that less than 60% of the carboxyl groups are dissociated (pH range 3-5.5). Although syringes are used to provide the shear mixing in this and the following examples, any shear-producing device which provides shear mixing can be used.

One ml of the lipophilic phase formed of the surfactant (and additives, when present) is placed in a 10 ml syringe and heated to 45° C., a temperature above the melting point of the surfactant. The lipophilic phase which results after the heating and blending of the lipophilic component(s) is forcibly injected, via a three-way stop-cock, into 4 ml of an aqueous phase. The aqueous phase (in this example, 4 mls of water) is contained in a 10 ml syringe, and is also at 45° C. The process of injection of the lipophilic phase into the aqueous phase takes less than five seconds. The resulting mixture is then forced repeatedly between the syringes at a linear flow rate of 8-12 m/s through an orifice about 1 mm in diameter. The mixture is driven continuously back and forth between the two syringes for approximately 2 minutes, providing the shear mixing necessary to make the paucilamellar lipid vesicles. A milky suspension containing the paucilamellar lipid vesicles results. The lipid vesicles are separated by centrifugation at 10,000 rpm for 15 minutes in a Beckman Instrumental Co. J-21 centrifuge, forming a low density phase on top of the aqueous solution.

TABLE 1

| Surfactant | C | $H_2O$ Uptake ml/g | Diameter (microns) |
|---|---|---|---|
| LS | + | 3.0 | 0.3 |
| LS | − | 4.0 | 0.45 |
| OS | + | 3.0 | 0.35 |
| OS | − | 4.0 | 0.60 |
| CS | + | 3.0 | 0.26 |
| CS | − | 2.5 | 0.40 |

Composition: surfactant/cholesterol = 33 mM/11 mM

As is evident from the results listed in Table 1, all of these surfactants form water-encapsulating vesicles in the presence or absence of cholesterol. The diameters and encapsulated volumes are greater when vesicles are formed with surfactants alone.

EXAMPLE 2

In this example, mineral oil (Drakeol 19) is used to show oil encapsulation efficiency for the paucilamellar lipid vesicles of this invention. As in the previous example, the surfactants tested are sarcosinamides of lauric acid, oleic acid and coconut oil fatty acids, and the lipophilic phase is formed with and without additives.

Table 2 lists the materials used, and the results. As in Table 1, the presence or absence of additives is indicated by +/−.

As in Example 1, the surfactant (and cholesterol, when present) is placed in a 10 ml syringe and heated to 45° C., a temperature above the melting point of the surfactant, forming 1 ml of the lipophilic phase. This surfactant mixture is then blended with different amounts of mineral oil in a series of experiments until post-encapsulation oil saturation is reached. The lipophilic phase of the lipid and oil is then blended with 4 ml of water, using the syringe method of Example 1.

As is evident from Table 2, all of these surfactants are able to encapsulate oil in the presence or absence of cholesterol and oleic acid. As in Example 1, diameters and volumes encapsulated are greater when vesicles are formed with surfactants alone.

TABLE 2

| Surfactant | C | Oil Uptake ml/g | Diameter (microns) |
|---|---|---|---|
| CS | + | 10 | 0.68 |
| CS | − | 18 | 0.84 |
| LS | + | 7 | 0.34 |
| LS | − | 12 | 0.50 |
| OS | + | 7 | 0.16 |

TABLE 2-continued

| Surfactant | C | Oil Uptake ml/g | Diameter (microns) |
|---|---|---|---|
| OS | − | 7 | 0.30 |

Composition: surfactant/cholesterol = 33 mM/11 mM

EXAMPLE 3

In this example, the ability of oleoyl propyl betaine to encapsulate water or mineral oil (Drakeol 19) is measured. Materials and proportions used are listed in Table 3.

TABLE 3

| Oleoyl propyl betaine | 33 mM |
|---|---|
| Cholesterol | 15 mM |
| 1 ml total lipid | |

The example is performed following essentially the same protocol as those of Examples 1 and 2. The aqueous phase is 2 mls water.

TABLE 4

| | Diameter ($\mu$) |
|---|---|
| $H_2O$ Uptake (ml/g) | |
| 1.5 | 0.15 |
| Oil Uptake (ml/g) | |
| 15-16 | ~1.9 |

The results, listed in Table 4, clearly show the ability of oleoyl propyl betaine to encapsulate aqueous or oil volumes.

The foregoing description is illustrative only and those skilled in the art may find other materials and methods which accomplish the same results. Such other materials are included within the following claims.

What is claimed is:

1. A method of preparing aqueous-filled, paucilamellar lipid vesicles consisting essentially of the steps of:
   A. Providing a solventless nonaqueous lipophilic phase comprising a single chain charge-localized nonphospholipid surfactant selected from the group consisting of betaines and anionic sarcosinamides and any lipid-soluble materials to be incorporated in said lipid vesicle;
   B. Providing an aqueous phase formed of an aqueous solvent and any aqueous soluble materials to be encapsulated; and
   C. Combining said nonaqueous lipophilic phase with a substantial excess of said aqueous phase in a single step under shear mixing conditions;
   whereby said aqueous-filled paucilamellar lipid vesicles are formed without the formation of a separable lamellar phase.

2. The method of claim 1 wherein said betaine comprises a betaine having the structure:

$$R_2-\overset{\overset{\displaystyle CH_3}{|}}{\underset{\underset{\displaystyle CH_3}{|}}{N^+}}-CH_2-\overset{\overset{\displaystyle O}{\|}}{C}-O^-$$

where $R_2$ is a long chain fatty acid ester.

3. The method of claim 2 wherein $R_2$ is propyl oleate, having the structure

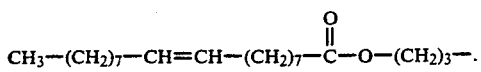

4. The method of claim 1 wherein said sarcosinamide comprises a sarcosinamide having the structure

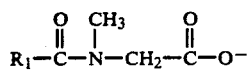

where

is the carbonyl derivative of a long chain fatty acid having 12 to 20 carbon atoms.

5. The method of claim 4 where $R_1$ is selected from the group consisting of lauric acid, fatty acids having 14-20 carbon atoms, and mixtures thereof.

6. The method of claim 1 wherein said lipophilic phase further comprises a sterol.

7. The method of claim 6 wherein said sterol comprises cholesterol.

8. The method of claim 1 wherein said lipophilic phase further comprises a charge-producing amphiphile.

9. The method of preparing oil-filled paucilamellar lipid vesicles having a water-immiscible oily material in their amorphous central cavities consisting essentially of the steps of:
   A. Providing a nonaqueous lipophilic phase comprising a charge-localized single chain nonphospholipid surfactant selected from the group consisting of betaines and anionic sarcosinamides and any lipid-soluble materials to be incorporated in said lipid vesicles;
   B. Providing an aqueous phase formed of an aqueous solvent and any aqueous soluble materials to be incorporated in said lipid vesicles; and
   C. Providing an oil phase of a water-immiscible oily material and any oil-dispersible material to be incorporated in said lipid vesicles;
   D. Blending said lipid phase and said oil phase to form a lipid-oil phase;
   E. Combining said lipid-oil phase with a substantial excess of said aqueous phase in a single step under shear mixing conditions;
   whereby said single chain charge-localized nonphospholipid paucilamellar lipid vesicles having a water-immiscible oily material in their central cavities are formed without the formation of a separable lamellar phase.

10. The method of claim 9 wherein said betaine comprises a betaine having the structure:

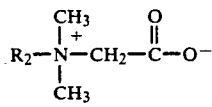

where $R_2$ is a long chain fatty acid ester.

11. The method of claim 10 wherein $R_2$ is propyl oleate, having the structure

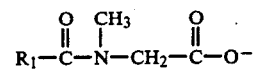

12. The method of claim 9 wherein said sarcosinamide comprises a sarcosinamide having the structure

where

is the carbonyl derivative of a long chain fatty acid having 12 to 20 carbon atoms.

13. The method of claim 12 where $R_1$ is selected from the group consisting of lauric acid, fatty acids having 14-20 carbon atoms, and mixtures thereof.

14. The method of claim 9 wherein said lipophilic phase further comprises a sterol.

15. The method of claim 14 wherein said sterol comprises cholesterol.

16. The method of claim 9 wherein said lipophilic phase further comprises a charge-producing amphiphile.

17. Aqueous-filled paucilamellar lipid vesicles consisting of 2-10 lipid bilayers in the form of substantially spherical shells separated by aqueous layers, said lipid bilayers comprising a charge-localized single chain nonphospholipid surfactant selected from the group consisting of betaines and anionic sarcosinamides as the primary lipid, and any lipid-soluble materials to be incorporated in said lipid vesicle bilayers.

18. The paucilamellar lipid vesicles of claim 12 wherein said betaine comprises a betaine having the structure:

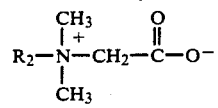

where $R_2$ is a long chain fatty acid ester.

19. The paucilamellar lipid vesicles of claim 18 wherein $R_2$ is propyl oleate, having the structure

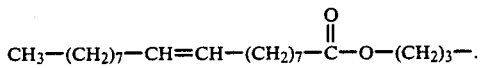

20. The paucilamellar lipid vesicles of claim 17 wherein said sarcosinamide comprises a sarcosinamide having the structure

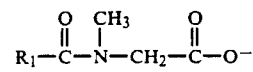

where

is the carbonyl derivative of a long chain fatty acid having 12 to 20 carbon atoms.

21. The paucilamellar lipid vesicles of claim 20 where $R_1$ is selected from the group consisting of lauric acid, fatty acids having 14–20 carbon atoms, and mixtures thereof.

22. The paucilamellar lipid vesicles of claim 17 wherein said lipophilic phase further comprises a sterol.

23. The paucilamellar lipid vesicles of claim 22 wherein said sterol comprises cholesterol.

24. The paucilamellar lipid vesicles of claim 17 wherein said lipophilic phase further comprises a charge-producing amphiphile.

25. Oil-filled paucilamellar lipid vesicles consisting of 2–10 lipid bilayers in the form of substantially spherical shells separated by aqueous layers, said lipid bilayers surrounding a substantially oil-filled amorphous central cavity, said lipid bilayers comprising a charge-localized single chain nonphospholipid surfactant selected from the group consisting of betaines and anionic sarcosinamides as the primary lipid, and any lipid-soluble materials to be incorporated in said lipid vesicle bilayers.

26. The paucilamellar lipid vesicles of claim 25 wherein said betaine comprises a betaine having the structure:

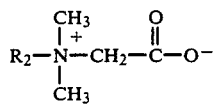

where $R_2$ is a long chain fatty acid ester.

27. The paucilamellar lipid vesicles of claim 26 wherein $R_2$ is propyl oleate, having the structure

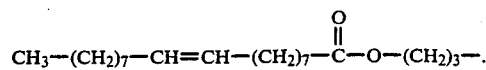

28. The paucilamellar lipid vesicles of claim 25 wherein said anionic sarcosinamide comprises a sarcosinamide having the structure

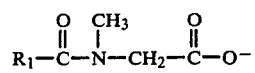

where

is the carbonyl group of a long chain fatty acid having 12 to 20 carbon atoms.

29. The paucilamellar lipid vesicles of claim 28 where $R_1$ is selected from the group consisting of lauric acid, fatty acids having 14–20 carbon atoms, and mixtures thereof.

30. The paucilamellar lipid vesicles of claim 25 wherein said lipophilic phase further comprises a sterol.

31. The paucilamellar lipid vesicles of claim 30 wherein said sterol comprises cholesterol.

32. The paucilamellar lipid vesicles of claim 25 wherein said lipophilic phase further comprises a charge-producing amphiphile.

* * * * *